United States Patent [19]

Kim et al.

[11] Patent Number: 5,426,212

[45] Date of Patent: Jun. 20, 1995

[54] SYNTHESIS OF α, ω-BIS(P-HYDROXYBENZOYLOXY) ALKANE

[75] Inventors: Ki-Soo Kim, Katonah, N.Y.; Sophia Dashevsky, Fair Lawn, N.J.; Stanley W. Palmaka, Yonkers, N.Y.

[73] Assignee: Akzo Nobel N.V., Arnhem, Netherlands

[21] Appl. No.: 112,632

[22] Filed: Aug. 26, 1993

Related U.S. Application Data

[63] Continuation of Ser. No. 779,478, Oct. 18, 1991, abandoned.

[51] Int. Cl.$^6$ .............................................. C07C 69/88
[52] U.S. Cl. ...................................................... 560/67
[58] Field of Search ......................................... 560/67

[56] References Cited

U.S. PATENT DOCUMENTS

| | | | |
|---|---|---|---|
| 4,536,593 | 8/1985 | Orban | 560/67 |
| 4,594,444 | 6/1986 | Orban | 560/67 |
| 4,716,244 | 12/1987 | Orban | 560/67 |

FOREIGN PATENT DOCUMENTS

| | | | |
|---|---|---|---|
| 52-39646 | 3/1977 | Japan | C07C 69/88 |
| 1578880 | 11/1980 | United Kingdom | C07C 69/84 |

OTHER PUBLICATIONS

Chemical Abstracts, vol. 87 (1977) 134692g.
Pp. 38 and 39 of European Patent Publication No. 450,652 (Oct. 9, 1991).
Chemical Abstracts, vol. 80 (1973) 96401g.
Kobunshi Kagaku, 30(9) 572–578 (1973).
C. Ober et al., "Liquid Crystal Polymers. V. Thermotropic Polyesters with Either Dyad or Triad Aromatic Ester Mesogenic Units and Flexible Polymethylene Spaces in the Main Chain", Polymer Journal, vol. 14, No. 1, pp. 9–17 (1982).

*Primary Examiner*—Paul J. Killos
*Attorney, Agent, or Firm*—Richard P. Fennelly; Louis A. Morris

[57] ABSTRACT

The reaction of methyl p-hydroxybenzoate and a α,ω-alkanediol, in the presence of a transesterification catalyst, such as a metal alkoxide and/or metal acetate, can be used to synthesize an α,ω-bis(p-hydroxybenzoyloxy)alkane monomer.

8 Claims, No Drawings

SYNTHESIS OF α,ω-BIS(P-HYDROXYBENZOYLOXY) ALKANE

This is a continuation of application Ser. No. 07/779,478, filed Oct. 18, 1991 is abandoned.

BACKGROUND OF THE INVENTION

It is known to form liquid crystal polymers containing a mesogenic triad unit with three linearly-aligned aromatic rings, the bis(p-carboxyphenyl) terephthalate moiety, and a polymethylene flexible spacer of varying length (e.g., from 2 to 10 $CH_2$ units). See Polymer Journal, Vol. 14, No. 1, pp. 9-17 (1982). One of the monomers used in building such a structure is the α,ω-bis(p-hydroxybenzoyloxy) alkane monomer of the following structure

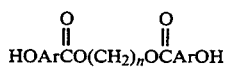

where Ar is a phenyl ring, n is from 2 to 10 and all linkages to the phenyl rings are para-. In those cases where n is 6 or 8, the flexible spacer group —$(CH_2)_n$ can be in cyclic form, i.e., cyclohexylene or cyclooctylene.

British Patent No. 1,578,880 at page 2, lines 15-27 indicates that phenols of the above type of structure can be made by esterifying p-hydroxybenzoic acid with ethylene glycol in either the presence or absence of a catalyst which may include toluenesulfonic acid. As illustrated by Comparative Example 3, below, this type of procedure in which p-toluenesulfonic acid is the catalyst yields a product of poor product purity.

DESCRIPTION OF THE INVENTION

The present invention involves formation of the α,ω-bis(p-hydroxybenzoyloxy) alkane monomer mentioned earlier by the transesterification reaction of two moles of methyl p-hydroxybenzoate with one mole of a α,ω-alkanediol in the presence of a transesterification catalyst. Transesterification catalysts of the metal alkoxide and metal acetate classes may be employed, either alone or in admixture. Representative catalysts are calcium acetate, cobalt acetate, zinc acetate, manganese acetate, and titanium (IV) butoxide. The selected alkanediol is responsible for insertion of the polymethylene spacer into the final monomer structure with the p-hydroxybenzoate monomer being responsible for the p-hydroxybenzoyloxy moieties bonded to the central alkane (polymethylene) spacer. The reaction is advantageously conducted neat without solvent at elevated temperatures (e.g., from about 150° C. to about 250° C.) with removal of by-product methanol. The transesterification catalyst can be present at from about 0.1% to about 5% by weight of the reactants, more preferably from about 0.5% to about 1.0%. An alkali metal acetate, alkaline earth metal acetate or mixtures can be used.

The present invention is further illustrated by the Examples which follow.

EXAMPLE 1

This illustrates the preparation of 1,4-bis(p-hydroxybenzoyloxy) butane in accordance with the present invention.

In a 50 ml flask, methyl p-hydroxybenzoate (15.2 gm, 0.1 mole), 1,4-butanediol (4.5 gm, 0.05 mole) and calcium acetate hydrate (0.2 gm) were added. The reaction mixture was then heated with stirring at 200°-240° C., and the methanol by-product was distilled off. After two hours heating, 4.0 ml of methanol (99% conversion) was collected. The reaction mixture was cooled and then 10 ml of methanol was added. The product was collected by filtration and was dried at 100° C. in a vacuum oven. It had a melting point of 175°-185° C. and a purity of 89% by GC. The product recrystallized from ethanol had a purity of 95% by GC and >90% by Mass spectroscopy.

EXAMPLE 2

Into a 100 ml flask were added, methyl p-hydroxybenzoate (30.4 gm, 0.2 mole), 1,4-butanediol (9.0 gm, 0.1 mole) and titanium (IV) butoxide (0.2 gm). The resulting reaction mixture was then heated, with stirring, at 210°-240° C. and methanol by-product was distilled off. After three hours of heating, a 65% conversion (4.2 gm of methanol) of the reactants was achieved.

COMPARATIVE EXAMPLE 3

This is presented for comparative purposes and illustrates preparation of the product of Example 1 by the direct reaction of p-hydroxybenzoic acid and 1,4-butanediol in tetrachloroethane using p-toluenesulfonic acid as a catalyst.

In a 250 ml flask, p-hydroxybenzoic acid (13.8 gm, 0.1 mole), 1,4-butanediol (4.5 gm, 0.05 mole), p-toluenesulfonic acid (0.9 gm) and tetrachloroethane (100 ml) were added. The reaction mixture was then refluxed, and the water by-product was collected using a reverse Dean Stark trap. After reaction for four and a half hours, 1.2 ml of water (70% conversion) was collected. The reaction mixture was filtered to remove the starting material. The filtrate was cooled and then the product (precipitate) was recovered. The analysis by gas chromatography showed the product had a purity of only 29%.

The foregoing are presented for illustrative purposes only and should therefore not be construed in a limiting sense. The scope of protection sought is set forth in the claims which follow.

We claim:

1. A method of synthesizing an α,ω-bis(p-hydroxybenzoyloxy) alkane which comprises reacting methyl p-hydroxybenzoate and a α,ω-alkanediol in the presence of a metal alkoxide transesterification catalyst.

2. A method as claimed in claim 1 wherein the metal acetate is titonium (IV) butoxide alkoxide.

3. A method as claimed in claim 1 wherein the catalyst is present at from about 0.1% to about 5%.

4. A method as claimed in claim 2 wherein the catalyst is present at from about 0.1% to about 5%.

5. A method as claimed in claim 1 wherein the α,ω-alkanediol has a $C_2$ to $C_{10}$ polymethylene structure.

6. A method as claimed in claim 2 wherein the α,ω-alkanediol has a $C_2$ to $C_{10}$ polymethylene structure.

7. A method as claimed in claim 3 wherein the α,ω-alkanediol has a $C_2$ to $C_{10}$ polymethylene structure.

8. A method as claimed in claim 4 wherein the α,ω-alkanediol has a $C_2$ to $C_{10}$ polymethylene structure.

* * * * *

UNITED STATES PATENT AND TRADEMARK OFFICE
CERTIFICATE OF CORRECTION

PATENT NO. : 5,426,212
DATED : June 20, 1995
INVENTOR(S) : Ki-Soo Kim, S. Dashevsky; S.W. Palmaka It is certified that error appears in the above—identified patent and that said Letters Patent is hereby corrected as shown below:

Col.2, line 52, "acetate" should read -- alkoxide--, "titonium" should read -- titanium--, and the word "alkoxide" after "butoxide" should be deleted.

Signed and Sealed this

Twenty-first Day of May, 1996

Attest:

BRUCE LEHMAN

Attesting Officer    Commissioner of Patents and Trademarks